United States Patent
Akahori

(10) Patent No.: US 11,035,811 B2
(45) Date of Patent: Jun. 15, 2021

(54) OBJECT DETERMINATION DEVICE, PROGRAM, OBJECT DETERMINATION METHOD, AND SEMICONDUCTOR DEVICE

(71) Applicant: LAPIS Semiconductor Co., Ltd., Yokohama (JP)

(72) Inventor: Hiroji Akahori, Yokohama (JP)

(73) Assignee: LAPIS SEMICONDUCTOR CO., LTD., Yokohama (JP)

( * ) Notice: Subject to any disclaimer, the term of this patent is extended or adjusted under 35 U.S.C. 154(b) by 134 days.

(21) Appl. No.: 16/386,981

(22) Filed: Apr. 17, 2019

(65) Prior Publication Data
US 2019/0331621 A1 Oct. 31, 2019

(30) Foreign Application Priority Data
Apr. 27, 2018 (JP) .............................. JP2018-087572

(51) Int. Cl.
*G01N 27/02* (2006.01)
*G01V 3/02* (2006.01)

(52) U.S. Cl.
CPC ............ *G01N 27/028* (2013.01); *G01V 3/02* (2013.01)

(58) Field of Classification Search
CPC ......... G01N 33/246; G01N 27/00; G01V 3/06
See application file for complete search history.

(56) References Cited

U.S. PATENT DOCUMENTS

2016/0313271 A1* 10/2016 Raupach ............... G01N 27/048
2017/0191951 A1* 7/2017 Lestelle ............... A01G 27/005
2017/0254766 A1* 9/2017 Bermudez Rodriguez ................
G01N 27/048

FOREIGN PATENT DOCUMENTS

JP 2013-200193 A 10/2013

* cited by examiner

*Primary Examiner* — Alvaro E Fortich
(74) *Attorney, Agent, or Firm* — Rabin & Berdo, P.C.

(57) ABSTRACT

An object-characteristic determination device includes a calculation unit and a determination unit. The calculation unit calculates a first feature value and a second feature value differing from the first feature value according to a first signal at a first frequency and a second signal at a second frequency. The first signal and the second signal are received by a reception unit after passing through the object. The first feature value and the second feature value represent features of the first signal and the second signal. The determination unit determines a property of the object on the basis of a difference in the first feature values of the first signal and a difference in the second feature values of the second signal, a relationship between a plurality of properties of the object, and a plurality of differences in the first feature values and a plurality of differences in the second feature values.

8 Claims, 11 Drawing Sheets

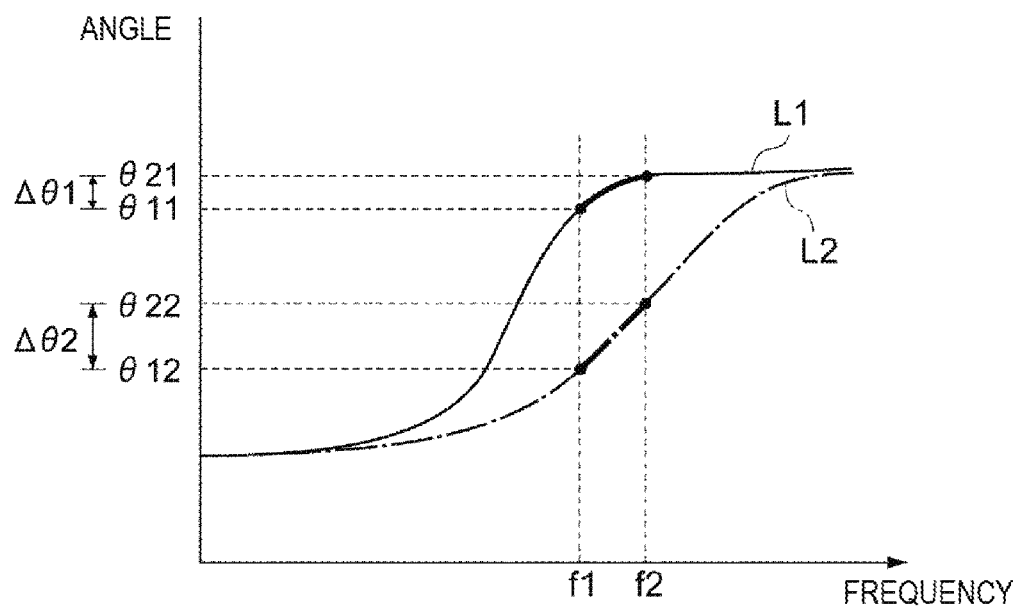

FIG. 6
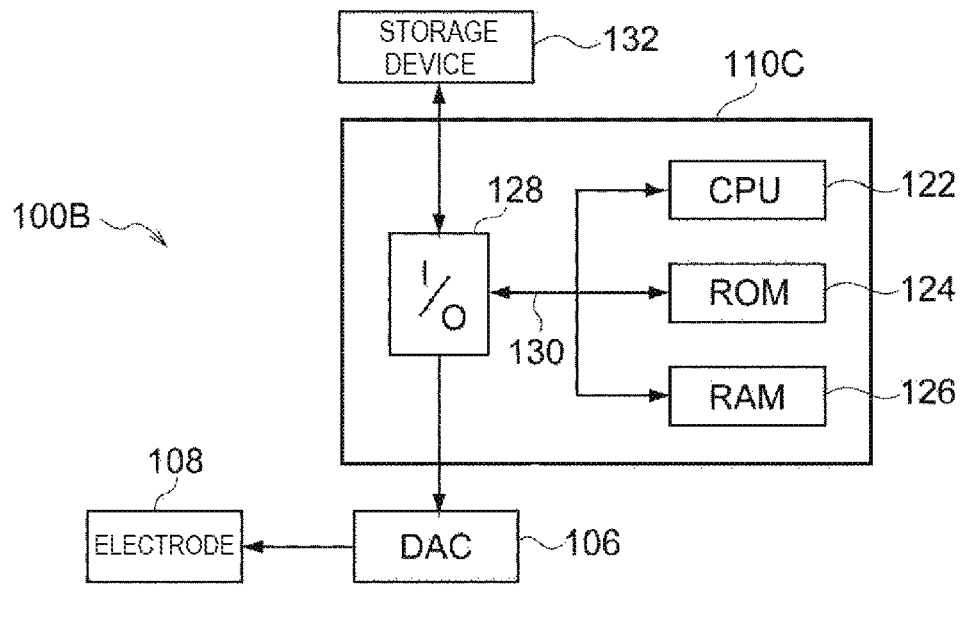
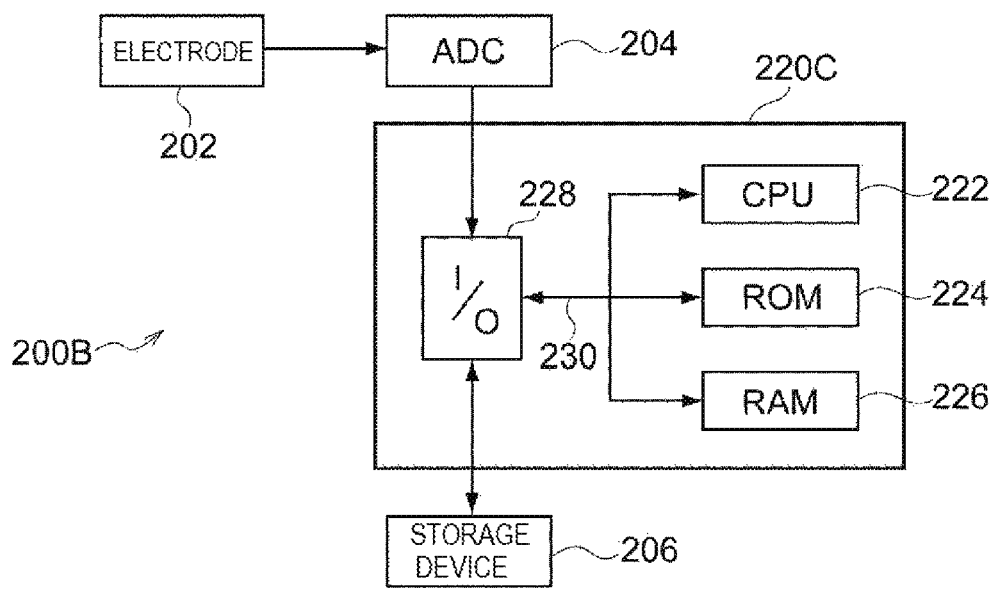

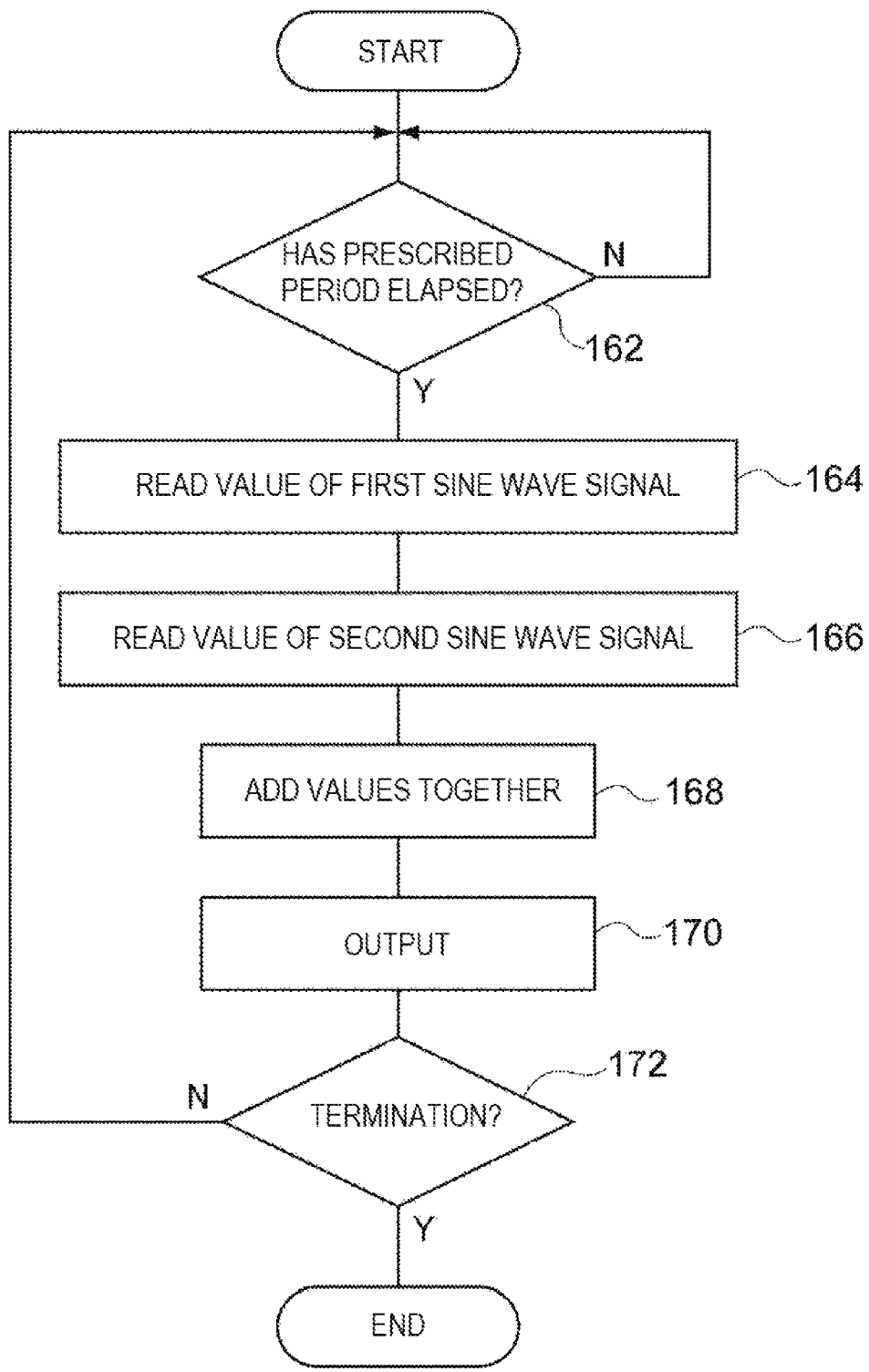

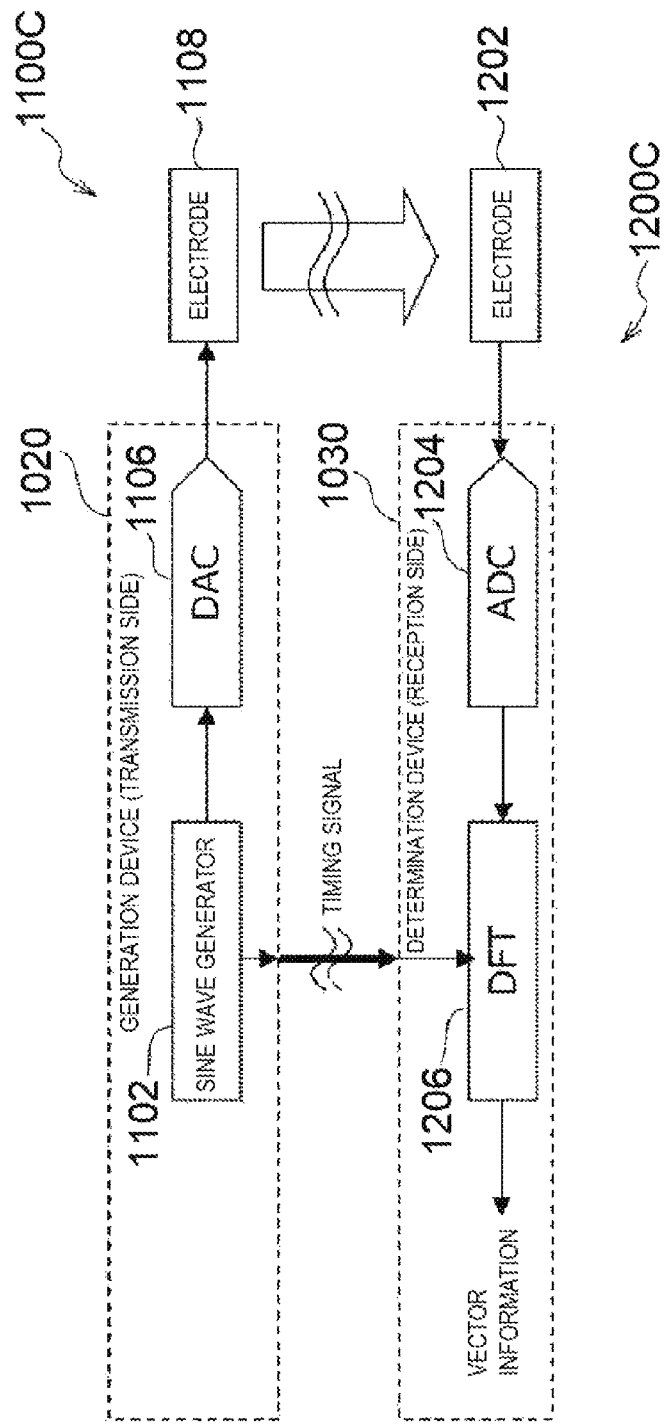

OBJECT DETERMINATION DEVICE, PROGRAM, OBJECT DETERMINATION METHOD, AND SEMICONDUCTOR DEVICE

TECHNICAL FIELD

The present invention relates to an object determination device, a program, and an object determination method.

BACKGROUND ART

Conventionally, in order to measure impedance as a property of soil, the moisture content of the soil and the ion concentration of the soil have been measured. In a conventional first ground determination device, electrodes are inserted into the soil, a signal at a desired frequency is transmitted from one of the electrodes, the transmitted signal (desired frequency) is received by the other electrode, and the impedance of the soil is measured on the basis of the received signal.

The impedance of soil includes, in addition to a resistance component, a capacitance component/induction component, and is expressed as a complex value. In acquiring a complex value, the reception side must have the phase timing of the signal at the desired frequency from the signal transmission side in order to have the degree to which the reception side phase needs to be rotated in relation to the transmission side (phase lag). Thus, in a conventional impedance measurement device, a signal is separately transmitted from the transmission side to the reception side in order for the reception side to have the timing information or timing of the transmission side.

Also, a conventional second ground determination device measures attenuation characteristics of the soil at the measured frequency by the reception side ascertaining in advance the level at which the transmission side transmitted the signal through some method, without using phase information.

Thus, in the conventional first and second ground determination devices, the timing information on the transmission side or some signal representing the timing, and a signal indicating the signal level are necessary. Therefore, if measuring the properties of the ground between two sensors respectively connected to the transmission side and the reception side, with the transmission side being separated from the reception side, a mechanism for transmitting, by wire or wirelessly, a timing signal pertaining to the phase on the transmission side, or a signal indicating the level on the transmission side, is necessary.

Conventionally, ground determination devices or systems configured in the manner of FIGS. 10A and 10B have been proposed, for example. Referring to FIG. 10A, a single generation/determination device 101 both generates and receives a signal. The device 101 includes a sine wave generator 1102, a digital-to-analog converter 1106, an electrode 1108 to transmit the generated sine wave, another electrode 1202 to receive the generated and transmitted sine wave through the ground, an analog-to-digital converter 1204, and a discrete Fourier transform (DFT) unit 1206. In such ground determination devices/systems, a DFT unit 1206 included on the reception side outputs the result of converting the phase and amplitude of the transmitted signal into a vector, and as described above, a timing signal is inputted from the transmission side. FIG. 10B is similar to FIG. 10A, except the sine wave generation 1102 and digital-to-analog conversion 1106 are performed by a generation device 1020 that is separate from the determination device 1030, and which includes the analog-to-digital conversion unit 1204 and the DFT unit 1206. Together, the generation device 1020 and the determination device 1030 make up a ground measurement system 1200C.

Japanese Patent Application Laid-Open Publication No. 2013-200193 is a related patent document.

SUMMARY OF THE INVENTION

However, if a wired mechanism is used for transmitting the timing signal pertaining to the phase on the transmission side or transmitting a signal indicating the level on the transmission side to the reception side, then a wiring material would be used to connect the transmission side and the reception side, which results in many restrictions such as reducing the installation flexibility of the respective devices on the transmission side and the reception side, the need to prevent disconnections resulting from falling or colliding objects when installing outdoors, and the need for a mechanism to prevent the induction of lightning, which increases installation and maintenance costs. This would also result in an increased amount of foreign objects in the soil such as wiring cables in the soil to be measured, which means that the effect on the measuring results due to cable installation must be taken into consideration. This results in a risk of not being able to attain the desired measurement results.

In the case of a wireless mechanism, there is no need for a cable, but it is difficult to acquire accurate timing information with an inexpensive wireless device due to transmission lag in wireless communication and restrictions on the wireless communication band.

The technique of the present disclosure takes into consideration such issues, and an object thereof is to provide an object determination device, a program, and an object determination method by which it is possible to determine the properties of an object without needing to receive a signal indicating the transmission timing of a first signal and a second signal.

An object determination method according to a first aspect of the technique of the present disclosure comprises: a calculation unit that, according to a first signal at a first frequency and a second signal at a second frequency differing from the first frequency that are received by a reception unit in a common state or separately through an object, calculates a first feature value and a second feature value differing from the first feature value that respectively represent features of the first signal and the second signal; and a determination unit that determines a property of the object on the basis of a difference in the first feature values and a difference in the second feature values of the first signal and the second signal, and a relationship between a plurality of properties of the object, and a plurality of differences in the first feature values and a plurality of differences in the second feature value.

An object determination method according to a second aspect of the technique of the present disclosure comprises: a step of, according to a first signal at a first frequency and a second signal at a second frequency differing from the first frequency that are received by a reception unit in a common state or separately through an object, calculating a first feature value and a second feature value differing from the first feature value that respectively represent features of the first signal and the second signal; and a step of determining a property of the object on the basis of a difference in the first feature values and a difference in the second feature values of the first signal and the second signal, and a relationship between a plurality of properties of the object, and a plurality of differences in the first feature values and a plurality of differences in the second feature value.

A program according to a third aspect of the technique of the present disclosure causes a computer to execute the object determination method.

An object determination method according to a fourth aspect of the technique of the present disclosure comprises: a storage device that stores a program for causing a processing device to execute the object determination method; and the processing device that executes the program stored in the storage device.

According to the present disclosure it is possible to determine the properties of an object without needing to receive a signal indicating the transmission timing of a first signal and a second signal.

BRIEF DESCRIPTION OF THE DRAWINGS

FIG. 4 is a graph showing the relationship between a signal frequency and a phase angle of the signal.

FIG. 5 shows a table in which the properties (L1, L2) of soil are identified and stored according to differences (ΔP1, ΔP2) between the powers (amplitude squared) at two differing frequencies, and differences (Δθ1, Δθ2) between the phase angles of the signals at the two differing frequencies.

FIG. 6 is a block diagram of a ground property determination system according to Embodiment 2.

FIG. 8 is a flowchart of a processing program by which the computer of the transmission device generates sine waves.

FIG. 10B is a block diagram of a ground determination system.

DETAILED DESCRIPTION OF EMBODIMENTS

Figure 1:
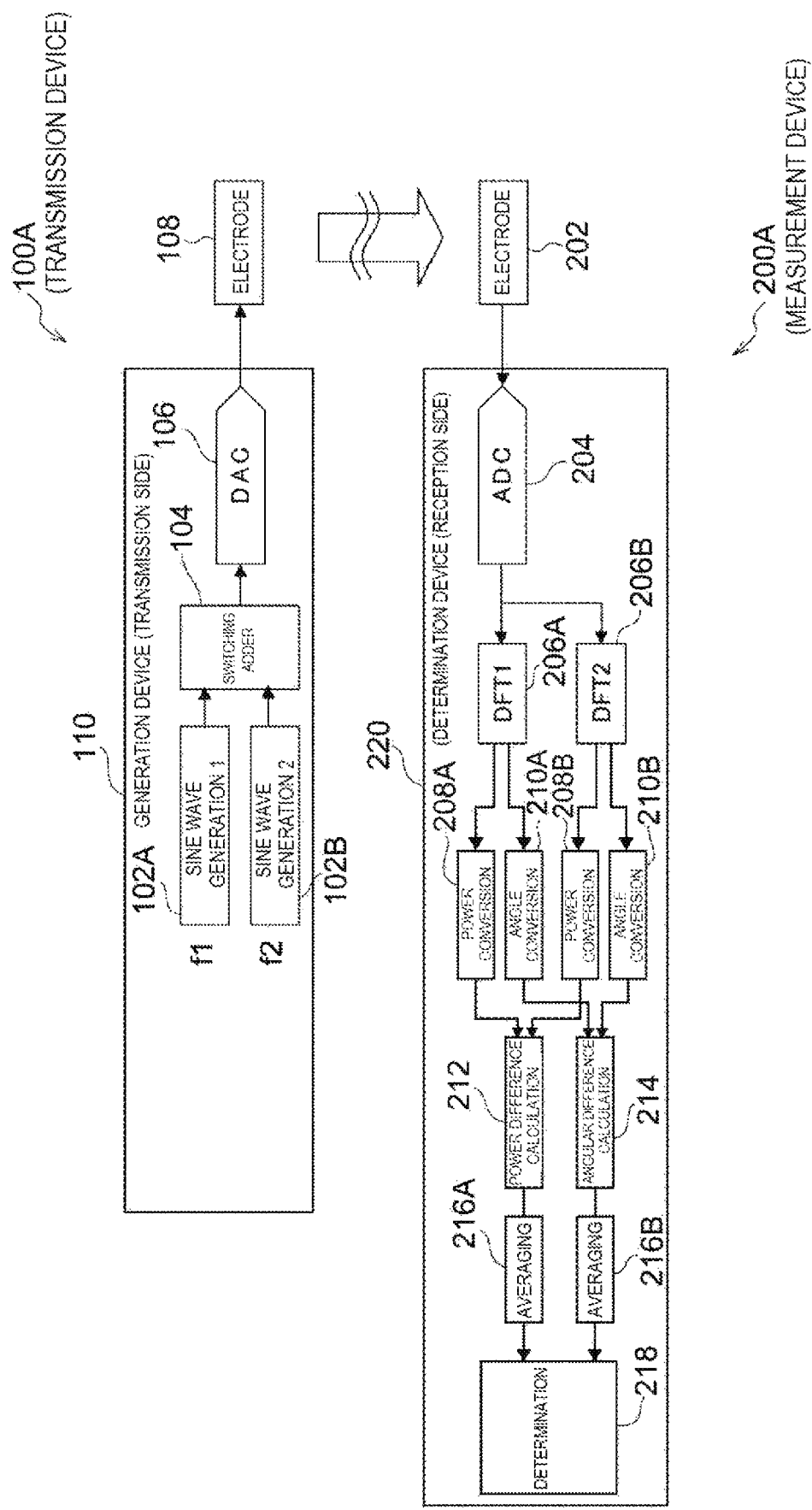
FIG. 1 is a block diagram of a ground property determination system according to Embodiment 1.

Examples of embodiments of a disclosed technique will be explained below with reference to the drawings. The same or equivalent components and portions in the drawings are assigned the same reference characters and redundant explanations thereof will be omitted.

Embodiment 1

FIG. 1 shows a ground property determination system. As shown in FIG. 1, the ground property determination system includes a transmission device 100A and a measurement device 200A. The transmission device 100A includes a generation device 110 and an electrode 108. The measurement device 100A includes an electrode 202 and a determination device 220. The electrode 108 and the electrode 202 are separated by a given distance (tens of centimeters to a few meters, for example), and, in an embodiment in which the object to be tested is the ground or soil, soil is present between the electrodes 108 and 202. The generation device 110 and the determination device 220 are constituted of semiconductor devices made up of processing circuitry and supporting electronic circuitry elements.

The determination device 220 is an example of an object determination device and a semiconductor device of the technique of the present disclosure. In the present specification and claims, the term "object" includes any discrete object, including organic or inorganic objects, manufactured objects, natural objects, the ground, such as soil or earth, as well as tissues, such as skin or other organic tissue.

The generation device 110 includes a sine wave generation circuit 102A and a sine wave generation circuit 102B. The sine wave generation circuit 102A generates a digital signal corresponding to a first sine wave at a first frequency f1 (hereinafter referred to as the "first sine wave signal"). The sine wave generation circuit 102B generates a digital signal corresponding to a second sine wave at a second frequency f2 (hereinafter referred to as the "second sine wave signal"). In Embodiment 1, the second frequency f2 is N times the first frequency f1. Embodiments of the present invention include any type of oscillator as the sine wave generation circuit 102A or 102B, whether formed as part of a processor chip, as a separate oscillator chip, or as any configuration of resistors, inductors, and capacitors, or in connection with a crystal oscillator, arranged to generate an oscillating sine wave at a predetermined frequency. The sine wave generation circuit 102A and the sine wave generation circuit 102B are connected to a switching adder circuit 104 that selectively switches between outputting the first sine wave signal and the second sine wave signal, or adds the sine wave signals together and simultaneously outputs the result. In Embodiment 1, the switching adder circuit 104 adds the first sine wave signal to the second sine wave signal and outputs the result as an added signal. In one embodiment, the switching adder circuit 104 may include one or more transistors configured as semiconductor switches. The switching adder circuit 104 is connected to a digital-to-analog converter (DAC) 106 that converts the added signal to analog and outputs the result as an electrical signal. The DAC 106 is connected to the electrode 108. The electrode 108 transmits the signal from the DAC 106 to the soil as an analog electrical signal.

The measurement device 200A includes the electrode 202, which receives the signal transmitted by the electrode 108 through the soil, and the determination device 220, which processes the signal received by the electrode 202 to determine the properties of the soil. The determination device 220 includes an analog-to-digital converter (ADC) 204 that is connected to the electrode 202 and converts the signal received by the electrode 202 into a digital signal. The ADC 204 has connected thereto a discrete Fourier transform (DFT) unit 206A that performs a discrete Fourier transform on the signal from the ADC 204 and outputs an amplitude and phase corresponding to the first sine wave (frequency f1), and a DFT unit 206B that performs a discrete Fourier transform on the signal from the ADC 204 and outputs an amplitude and phase corresponding to the second sine wave (frequency f2). In embodiments of the invention, the DFT units 206A and 206B may include a processor processing instructions stored in memory to process the signal from the ADC 204 and to perform the discrete Fourier transform on the signal.

The DFT unit 206A has connected thereto a power conversion circuit 208A and an angle conversion circuit 210A. The DFT unit 206B has connected thereto a power conversion circuit 208B and an angle conversion circuit 210B. The power conversion circuit 208A squares the amplitude from the DFT unit 206A to convert the amplitude to power. The angle conversion circuit 210A converts the phase from the DFT unit 206A to an angle. The power conversion circuit 208B squares the amplitude from the DFT unit 206B to convert the amplitude to power. The angle conversion circuit 210B converts the phase from the DFT unit 206B to an angle. In embodiments of the present invention, the power conversion circuits and angle conversion circuits may be made up of one or more processors executing instructions from memory, as well as supporting logic or circuitry, to covert values corresponding to amplitudes to values corresponding to power, and to convert values corresponding to phase to values corresponding to angles.

The power conversion circuits 208A and 208B are connected to a power difference calculation circuit 212. The power difference calculation circuit 212 calculates the power difference between the power conversion circuits 208A and 208B. The angle conversion circuits 210A and 210B are connected to an angular difference calculation circuit 214. The angular difference calculation circuit 214 calculates the angular difference between the angle conversion circuits 210A and 210B.

The power difference calculation circuit 212 is connected to an averaging circuit 216A that calculates the average of the power differences calculated by the power difference calculation circuit 212. The angular difference calculation circuit 214 is connected to an averaging circuit 216B that calculates the average of the angular differences calculated by the angular difference calculation circuit 214. The averaging circuits 216A and 216B are connected to a determination circuit 218. The determination circuit 218 includes a table indicating the relationship between the power difference and angular difference to be described in detail later, and the properties of the soil (see FIG. 5).

The determination circuit 218 determines the properties of the soil between the electrodes 108 and 202 on the basis of the power difference and angular difference that have been averaged by the averaging circuits 216A and 216B, and the relationship between the power difference and angular difference, and the properties of the soil in the table. In Embodiment 1, properties of the soil include the pH of the soil and the moisture content per unit volume of the soil. The properties of the soil are not limited to the pH and moisture content, but may include the ion concentration instead of or in addition to the pH and moisture content, for example.

Components from the DFT unit 206A to the averaging circuit 216B constitute an example of the calculation unit of the technique of the present disclosure. The determination circuit is an example of the determination unit of the technique of the present disclosure. The amplitude and phase generated by the DFT units 206A and 206B are examples of feature values of first and second signals, where the first and second sine waves (at frequency f1 and f2) constitute different signals that are carried within a signal detected or received by the electrode 202. For example, the amplitude value output by the DFT unit 206A may correspond to a value of a first feature of the measured object and the amplitude value output by DFT unit 206B may correspond to another value of the first feature. Likewise, the phase value generated by the DFT unit 206A may correspond to a value of a second feature of the measured object and the phase value generated by the DFT unit 206B may correspond to another value of the second feature of the measured object.

Next, the operation of the Embodiment 1 will be explained.

First, the operation of the transmission device 100A will be explained. The sine wave generation circuit 102A of the generation device 110 generates the first sine wave signal, and the sine wave generation circuit 102B generates the second sine wave signal. The timing at which the sine wave generation circuit 102A starts generating the first sine wave signal is the same as the timing at which the sine wave generation circuit 102B generates the second sine wave signal. The first sine wave signal has the same amplitude as the second sine wave signal. The switching adder circuit 104 adds the first sine wave to the second sine wave outputted from the sine wave generation circuits 102A and 102B, and outputs the result as an added signal. The DAC 106 converts the added signal from the switching adder circuit 104 to an analog signal and outputs the result to the electrode 108. The electrode 108 transmits the signal outputted from the DAC 106 to the soil.

Next, the operation of the measurement device 200A will be explained. The signal transmitted to the soil as described above is received by the electrode 202 of the measurement device 200A, and the electrode 202 outputs the received signal to the ADC 204. The ADC 204 converts the received signal into a digital signal, and outputs the resulting signal to the DFT units 206A and 206B.

The DFT units 206A and 206B perform DFT on the signal received over a given period of time. The number of signals to subject to DFT by the DFT units 206A and 206B differs between the DFT unit 206A and the DFT unit 206B, but the DFT units 206A and 206B use signals received during the same period of time. This period of time is the least common multiple of the period determined by the wavelength of the first sine wave signal at the first frequency f1 and the period determined by the wavelength of the second sine wave signal at the second frequency f2. The reason that the DFT units 206A and 206B use signals received over the same period is in order to reduce the effect of disturbance noise. If the DFT unit 206A were to use signals received during a first period and the DFT unit 206B were to use signals received during a second period that is longer than the first period, then if disturbance noise occurs after the first period elapses but before the second period has elapsed, the disturbance noise would only affect the amplitude and phase acquired from the DFT unit 206B.

Another reason that the DFT units 206A and 206B use signals received over the same period is in order to reduce susceptibility to noise. More specifically, if the DFT unit 206A were to use signals received during a first prescribed period and the DFT unit 206B were to use signals received during a second prescribed period that directly follows the first prescribed period, then compared to a case in which the DFT units 206A and 206B both use signals received during the first prescribed period, a longer period of time would be taken as a result of the inclusion of the second prescribed period, which increases the probability disturbance noise having an effect on the signals. However, in the present embodiment, the DFT units 206A and 206B use signals received over the same period, and thus, susceptibility to noise can be reduced.

Also, the present embodiment makes a determination regarding characteristics of an object, such as the characteristics of soil, using the difference in power levels attained by converting the amplitudes from the DFT units 206A and 206B, and by using the difference in phase angles from the DFT units 206A and 206B. The DFT units 206A and 206B use signals received during the same period, and thus, even if there were disturbance noise during the same period, then the differences in power and differences in angle would be affected similarly by the noise, and thus, the effect of noise can be reduced.

The DFT unit 206A performs a first DFT process using a prescribed number of signals every time a prescribed number of signals from the ADC 204 are accumulated, and outputs, to the power conversion circuit 208A and the angle conversion circuit 210A, signals indicating the amplitude and the phase of the first sine wave signal at the first frequency f1. The DFT unit 206B performs a second DFT process using a prescribed number of signals every time a prescribed number of signals from the ADC 204 are accumulated, and outputs, to the power conversion circuit 208B and the angle conversion circuit 210B, signals indicating the amplitude and the phase of the second sine wave signal at the second frequency f2.

The first DFT process and the second DFT process respectively include a process of DFT conversion and a process for determining the amplitude and phase.

As described above, the timing at which the sine wave generation circuit 102A of the generation device 110 starts generating the first sine wave signal is the same as the timing at which the sine wave generation circuit 102B generates the second sine wave signal. The operation timing is the same for the DFT units 206A and 206B.

The power conversion circuits 208A and 208B calculate the square of the received amplitude to convert the amplitude to a power value. The angle conversion circuits 210A and 210B convert the received phase to an angle.

The power difference calculation circuit 212 calculates the difference in power value between the power conversion circuits 208A and 208B. The angular difference calculation circuit 214 calculates the difference in angle between the angle conversion circuits 210A and 210B.

As described above, the DFT units 206A and 206B output, to the power conversion circuits 208A and 208B and the angle conversion circuits 210A and 210B, signals indicating the amplitude and the phase every time a prescribed number of signals are accumulated from the ADC 204. Thus, components from the DFT unit 206 to the angular difference calculation circuit 214 operate, as described above, every time a prescribed number of signals are accumulated by the DFT units 206A and 206B, or in other words, every prescribed period of time. The averaging circuit 216A has inputted thereto the power difference from the power difference calculation circuit 212 every prescribed period of time, and the averaging circuit 216B has inputted thereto the angular difference from the angular difference calculation circuit 214 every prescribed period of time. Once the number of power value differences from the power difference calculation circuit 212 reaches a certain number, the averaging circuit 216A calculates the average of the power differences. Once the number of angular differences from the angular difference calculation circuit 214 reaches a certain number, the averaging circuit 216B calculates the average of the angular differences.

The determination circuit 218 determines the properties of the soil (such as pH and moisture content) on the basis of the average of the power differences from the averaging circuit 216A and the average of the angular differences from the averaging circuit 216B.

Next, the principle by which the properties of the soil (such as pH and moisture content) can be determined on the basis of the power differences and the angular differences will be described.

Figure 2:
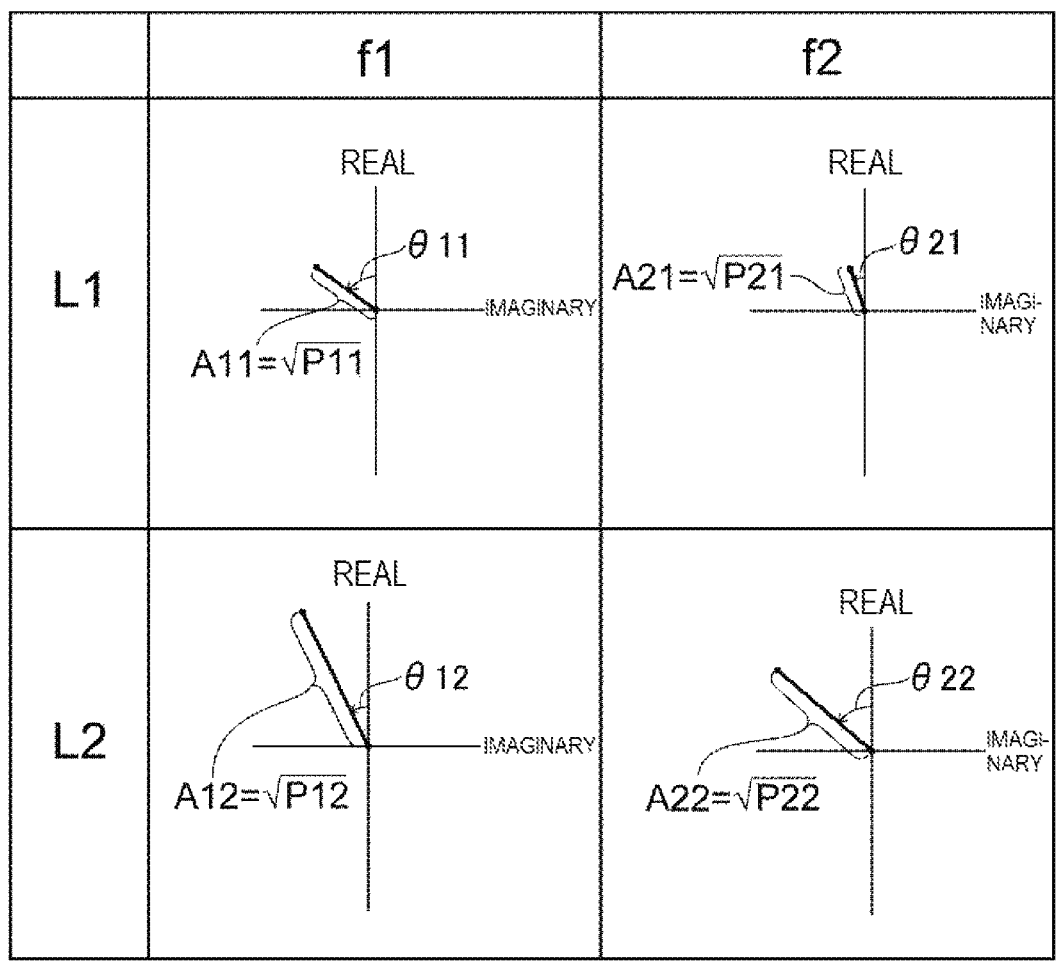
FIG. 2 indicates by vectors a relationship between amplitudes A11 to A22 and phases θ11 to θ22 for a case in which signals of a first frequency f1 and a second frequency f2 transmitted through soil of a first property L1 and ground of a second property L2 are respectively subjected to first discrete Fourier transform (DFT) processing and second DFT processing.

FIG. 2 indicates by vectors a relationship between amplitudes A11 to A22 and phases θ11 to θ22 for a case in which signals of a first frequency f1 and a second frequency f2 transmitted through soil of a first property L1 and ground of a second property L2 are respectively subjected to first DFT processing and second DFT processing.

As shown in FIG. 2, the amplitudes A11 to A22 and the phases θ11 to θ22 are determined by a vector of "real number+j×imaginary number". By the respective DFT conversions of the first and second DFT processes, a vector (real number, imaginary number) is determined. The real number is "amplitude×cos(phase)", the imaginary number is "amplitude×sin(phase)", the power is "(real number)$^2$+(imaginary number)$^2$", and the amplitude is "$\sqrt{}$(power)=$\sqrt{}$((real number)$^2$+(imaginary number)$^2$)". Thus, the amplitude is determined by $\sqrt{}$((real number)$^2$+(imaginary number)$^2$).

Also, the real number=amplitude×cos(phase), and thus, cos(phase)=(real number/amplitude). Thus, the phase is acos (real number/amplitude). Also, the imaginary number=amplitude×sin(phase), and thus, sin(phase)= (imaginary number/amplitude). Thus, the phase is also asin (real number/amplitude). Thus, the phase is determined by acos(real number/amplitude) or asin(imaginary number/amplitude). The phases θ11 to θ22 represent the timing at which the signal from the transmission device 100A is transmitted with reference to the real number axis.

Thus, the amplitudes A11 to A22 and the phases θ11 to θ22 are determined according to the vector (real number, imaginary number) attained by DFT. In the first and second DFT processes of the present embodiment, the amplitude and phase are further determined from the vector (real number, imaginary number) attained by DFT.

If the soil between the electrodes 108 and 202 has a first property L1, then if the first DFT process is executed for a signal at the first frequency f1, then the amplitude A11 and the phase θ11 are outputted, and if the second DFT process is executed for an electrical signal at the second frequency f2, then the amplitude A21 and the phase θ21 are outputted. If the soil between the electrodes 108 and 202 has a second property L2, then by the first DFT process, the amplitude A12 and the phase θ12 are outputted, and by the second DFT process, the amplitude A22 and the phase θ22 are outputted.

Thus, the reason that the amplitude and phase angle differ as in (A11, A12), (A21, A22), (θ11, θ12), and (θ21, θ22) despite the frequency being the same and the same DFT process being executed is that the properties of the soil differ.

Figure 3:
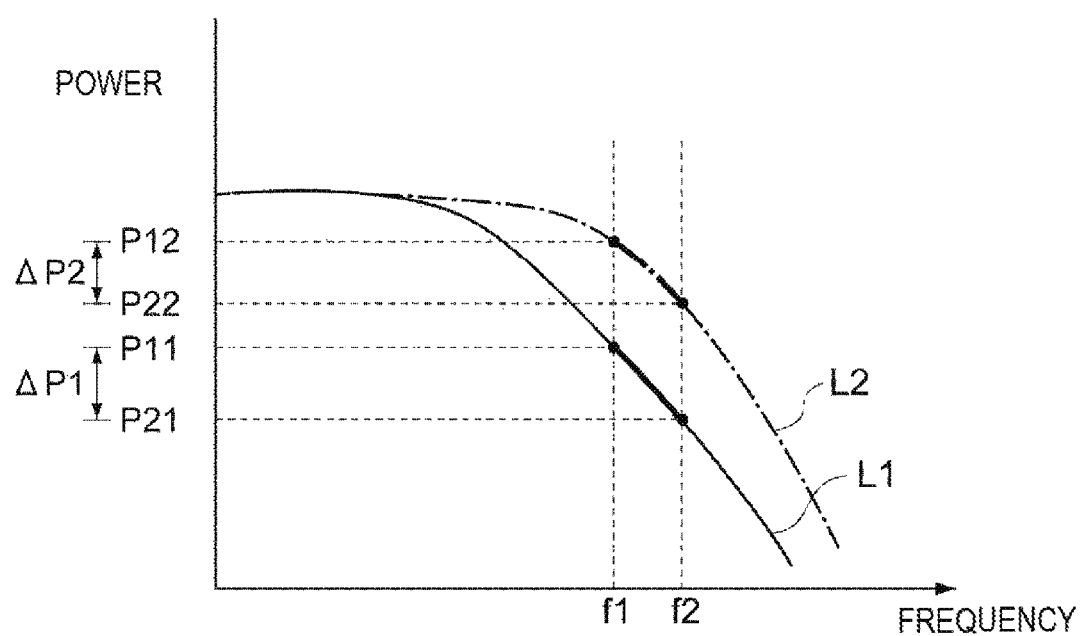
FIG. 3 is a graph showing the relationship between a signal frequency and the power attained by squaring the amplitude of the signal.

FIG. 3 shows the relationship between a signal frequency and the power attained by squaring the amplitude of the signal. As shown in FIG. 3, the power attained by squaring the amplitude differs depending on the frequency and whether the soil between the electrodes 108 and 202 has a property L1 or L2. The vertical axis in FIG. 3 is logarithmic. FIG. 4 shows the relationship between a signal frequency and a phase angle of the signal. As shown in FIG. 4, the angle of the signal phase differs depending on the frequency and whether the soil between the electrodes 108 and 202 has the property L1 or L2.

Conversely, the difference in power (amplitude squared) of the signals at the two different frequencies f1 and f2, ΔP1 (P11-P21) and ΔP2 (P12-P22), differs depending on the property L1 or L2 of the soil. Also, the difference in phase angle of the signals at the two different frequencies f1 and f2, Δθ1 (θ11-θ21) and Δθ2 (θ12-θ22), differs depending on the property L1 or L2 of the soil.

In other words, if the soil properties differ, the difference in power (amplitude squared) and difference in phase angle of signals at the two different frequencies f1 and f2 differ, and thus, if the difference in power (amplitude squared) and phase angle of the signals at the two different frequencies f1 and f2 are determined, the properties of the soil are identified. FIG. 5 shows a table in which the properties (L1, L2) of soil are identified and stored according to differences (ΔP1, ΔP2) between the powers (amplitude squared) at two differing frequencies, and differences (Δθ1, Δθ2) between the angles of the signal phases at the two differing frequencies.

Thus, it is possible to determine the properties of the soil between the electrodes 108 and 202 on the basis of the differences (ΔP1, ΔP2) between the powers (amplitude squared) at the two differing frequencies, the differences (Δθ1, Δθ2) between the angles of the signal phases at the two differing frequencies, and the table.

If the determined difference in power values and difference in angles does not correspond to a value set in the table, then the closest value is selected, and the properties of the soil are determined according to the selected value.

As described above, in Embodiment 1, the properties of the soil can be determined.

In determining the moisture content (per unit volume) as a property of the soil, if the electrodes 108 and 202 are to be embedded in a cliff of a mountain or the like, it is possible to determine the probability of the cliff collapsing according to the determined water content, and Embodiment 1 can be used as a landslide warning system that issues an advisory, a warning, or the like if the determined moisture content exceeds a threshold indicating a predetermined likelihood of a landslide occurring. Also, Embodiment 1 can be used as a plant growth system that can ascertain the moisture content of soil surrounding crop seeds or the like that have been planted in the soil if the electrodes 108 and 202 are embedded in the location where the seeds are planted, where if the moisture content falls below a threshold, an irrigation system is activated.

Also, the DFT unit 206A performs the first DFT process and outputs the amplitude and phase of the first sine wave signal at the first frequency f1, and the DFT unit 206B performs the second DFT process and outputs the amplitude and phase of the second sine wave signal at the second frequency f2. Thus, the DFT units 206A and 206B can determine the amplitudes of the first sine wave signal and the second sine wave signal, and thus, there is no need to transmit/receive a signal indicating information of the transmission signal level between the generation device 110 and the determination device 220. Also, the time difference (timing lag) between when the signal is transmitted from the transmission device 100A and when the signal is received by the measurement device 200A corresponds to the phase difference. As described above, the DFT units 206A and 206B determine the phases of the first sine wave signal and the second sine wave signal, and thus, it is also possible to determine the time difference (time lag) between the times when the first sine wave signal and the second sine wave signal are received by the measurement device 200A. Thus, there is no need to transmit/receive, between the generation device 110 and the determination device 220, a timing signal pertaining to the phase of the signal generated by the generation device 110. As described above, in Embodiment 1, it is possible to determine the properties of soil without a communication path for transmitting/receiving a timing signal pertaining to the phase of the signal generated by the generation device 110 or a signal indicating level information of the transmission signal.

If a time difference occurs between the first transmission signal corresponding to the first sine wave signal and the second transmission signal corresponding to the second sine wave signal and these signals are separately transmitted/received, then if either the first transmission signal or the second transmission signal is affected by external noise, then a large error would occur in the power difference and phase difference. However, in Embodiment 1, the switching adder circuit 104 of the transmission device 100A adds the first sine wave signal to the second sine wave signal and outputs the result as an added signal. Even if external noise were to have an effect on the added signal, the error on the power difference and phase difference would be relatively small. Thus, in Embodiment 1, it is possible to accurately determine the properties of soil even if external noise affects the signal transmitted/received.

Also, the switching adder circuit 104 of the transmission device 100A adds the first sine wave signal to the second sine wave signal and outputs the result as an added signal, and thus, the need for timing control or the like between the first sine wave signal and the second sine wave signal is obviated.

Embodiment 2

Next, Embodiment 2 will be explained. FIG. 6 shows a ground property determination system. A transmission measurement system includes a transmission device 100B and a measurement device 200B. The transmission device 100B includes an electrode 108, a DAC 106, a storage device 132, and a computer 110C. The computer 110C is configured such that a CPU 122, a ROM 124, a RAM 126, and an input/output (I/O) port 128 are connected to each other via a bus 130. The I/O 128 is connected to the storage device 132 and the DAC 106, and the DAC 106 is connected to the electrode 108. The storage device 132 stores a processing program that generates sine waves to be described later, and information of waveforms of a sine wave signal at a first frequency f1 and a sine wave signal at a second frequency f2.

The measurement device 200B includes an electrode 202, an ADC 204, a storage device 206, and a computer 220C. The computer 220C is configured such that a CPU 222, a ROM 224, a RAM 226, and an input/output (I/O) port 228 are connected to each other via a bus 230. The input/output (I/O) port 228 is connected to the ADC 204 and the storage device 206. The ADC 204 is connected to the electrode 202. The storage device 206 has stored therein a determination processing program to be described later. While the storage device 206 is illustrated as being separated from the CPU 222, ROM 224, and RAM 226, the determination processing program may be stored in one or more locations, including each of the storage device 206, ROM 224, and RAM 226, and the determination processing program may be carried out by one or more processors of the CPU 222. In an alternative embodiment, the storage device 206 may include independent processors or other circuitry to perform the determination processing independently of the CPU 222. The storage device 206 may be the physical storage of the processing program that defines the operation of the discrete Fourier transform (DFT) units 206A and 206B.

The computer 220C is an example of an object determination device of the technique of the present disclosure. The determination processing program is an example of the program of the technique of the present disclosure.

Figure 7A:
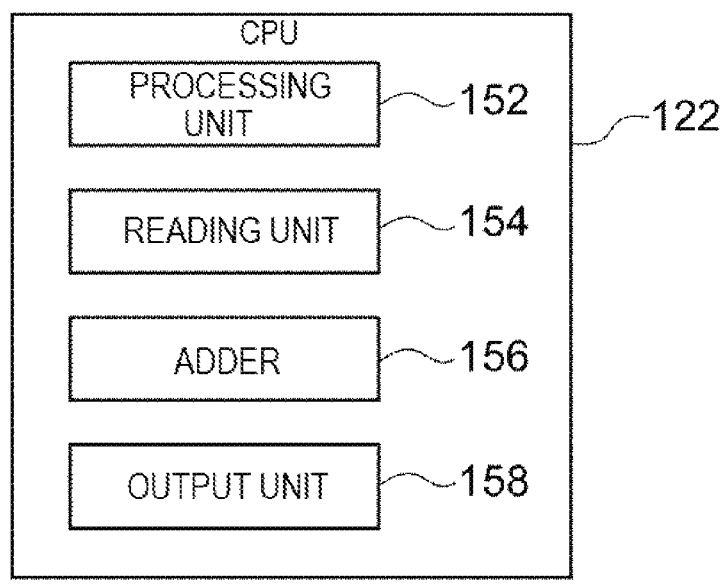
FIG. 7A shows functional units of a central processing unit (CPU) of a computer of a transmission device.

FIG. 7A shows functional units of the CPU 122 of the computer 110C. The CPU 122 includes a processing unit 152, a reading unit 154, an adder 156, and an output unit 158.

Figure 7B:
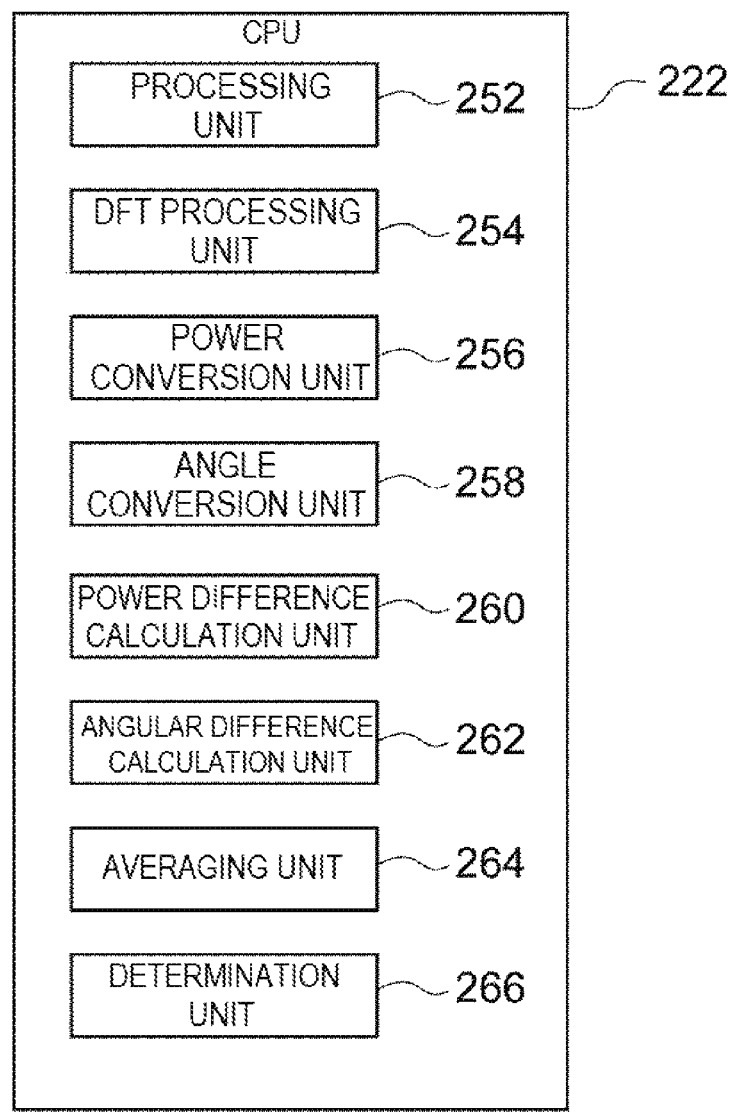
FIG. 7B shows functional units of a CPU of a computer of a receiving device.

FIG. 7B shows functional units of the CPU 222 of the computer 220C. The functional units of the CPU 222 include a processing unit 252, a DFT processing unit 254, a power conversion unit 256, an angle conversion unit 258, a power difference calculation unit 260, an angular difference calculation unit 262, an averaging unit 264, and a determination unit 266. In the present embodiments, the functional units of the CPU 122 and the CPU 222 may be made up of one or more processors and processing circuitry, or other logic circuitry, configured with particular hardware, including transistor circuitry and passive electrical devices, such that the CPUs 122 and 222 execute the functions of the respective functional units upon receiving particular instructions and data from memory, such as the ROM 124, 224 or RAM 126, 226. The CPUs 122 and 222 may be configured with two or more processors to perform different processing operations simultaneously, with one or more processors that are configured to perform multi-thread processing, or with any other processing scheme or structure to permit the CPUs 122 and 222 to perform the functions of the respective functional units.

FIG. 8 shows a flowchart of the processing program by which the computer 110C of the transmission device 100B generates a sine wave. The processing performed by the processing program shown in FIG. 8 that generates a sine wave is similar to the generation performed by the generation device 110 of Embodiment 1, and thus, detailed descriptions thereof are omitted.

In step 162, the processing unit 152 determines whether or not a prescribed period of time has elapsed since the processing program started or a signal to be described later has been outputted. If the prescribed period is determined not to have elapsed, then the processing program stands by until the prescribed period elapses.

If it is determined that a prescribed period has elapsed, in step 164, the reading unit 154 reads the value of a first sine wave signal corresponding to the timing from the storage device 132, and in step 166, the reading unit 154 reads the value of the second sine wave signal corresponding to the timing from the storage device 132.

In step 168, the adder 156 adds the values read in steps 164 and 166, and in step 170, the output unit 158 outputs the added value to the DAC 106. The DAC 106 converts the added signal to analog and then outputs the result to the electrode 108. The electrode 108 outputs (transmits) the signal to the soil.

In step 172, the processing unit 152 determines whether or not a termination command has been inputted from an input unit (not shown). If a termination command has not been inputted, the process returns to step 162, and the above processes (steps 162 to 172) are executed. If the termination command has been inputted, then the processing program, which generates sine waves, is terminated.

The signal outputted from the electrode 108 as described above is received through the soil by the electrode 202 of the measurement device 200A. Every time the electrode 202 receives a signal, the ADC 204 converts the received signal to digital and inputs the result to the computer 220C.

Figure 9:
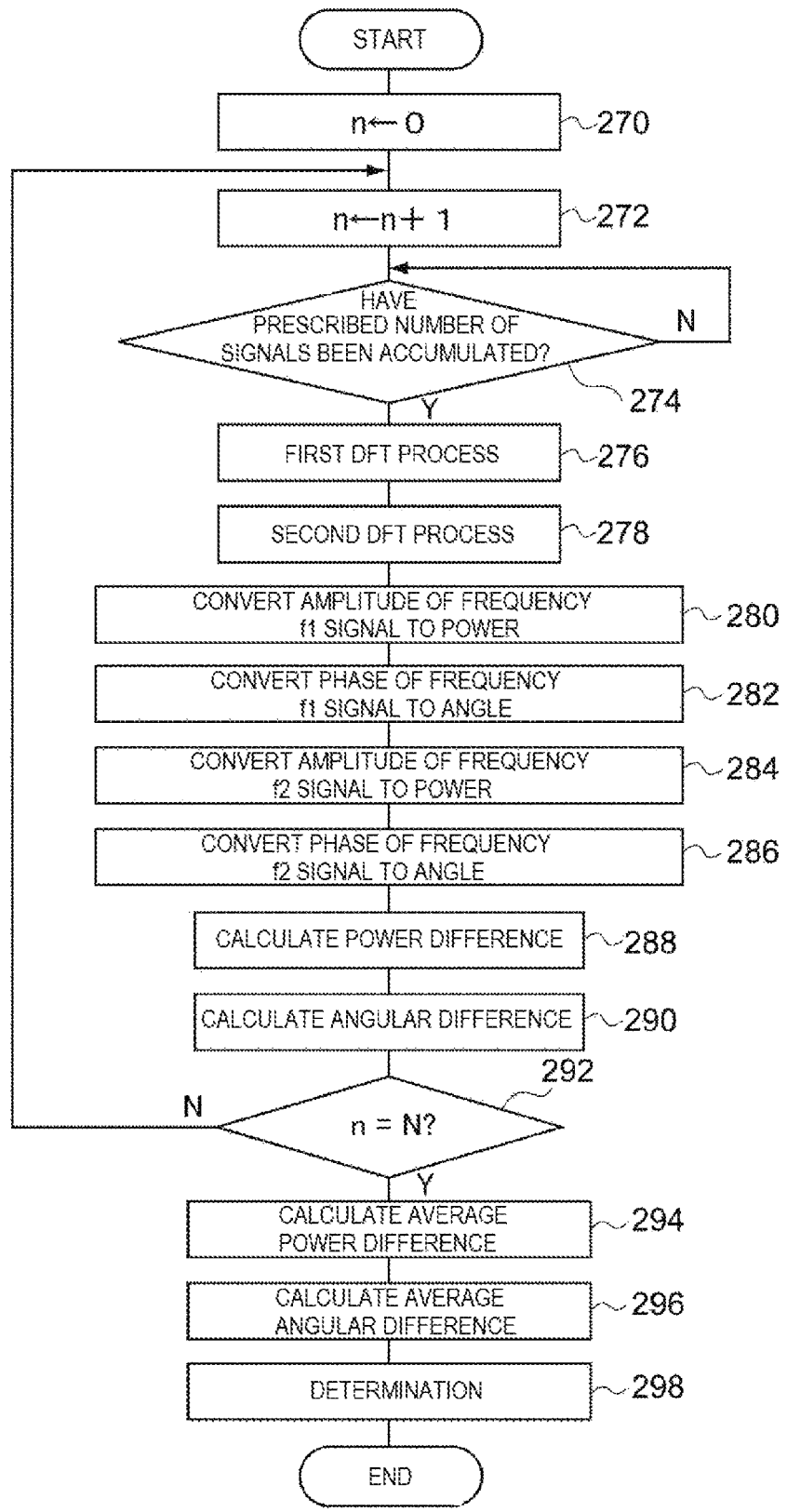
FIG. 9 is a flowchart of a determination processing program for a measurement device 200B to determine the properties of soil.
Figure 10A:
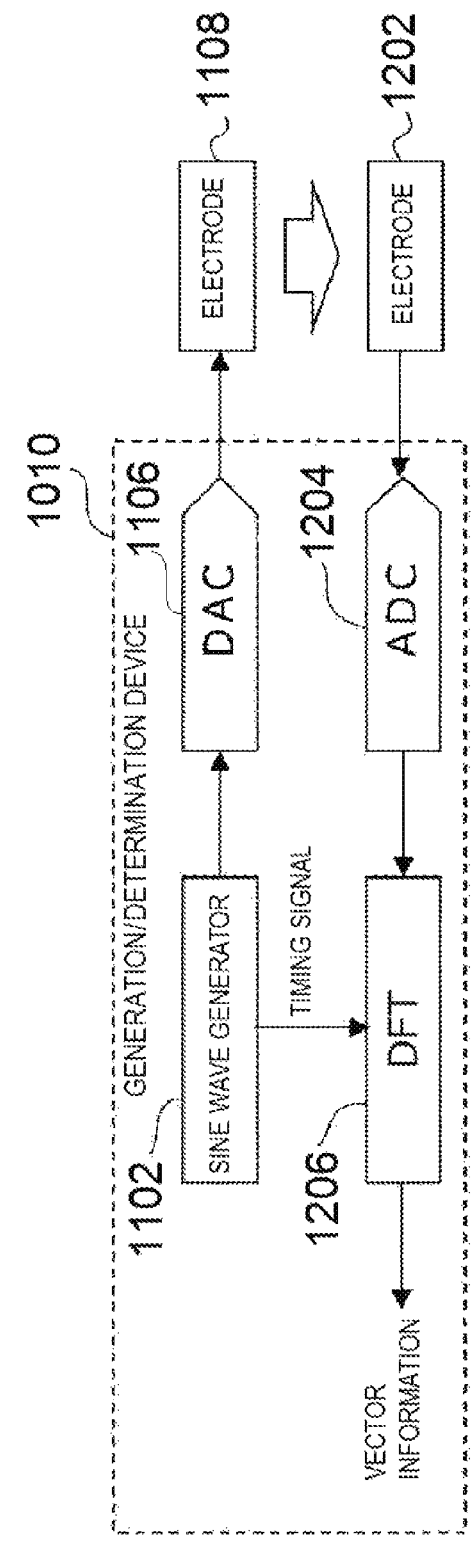
FIG. 10A is a block diagram of a ground determination device.

FIG. 9 shows a flowchart of the determination processing program for the measurement device 200B to determine the properties of soil. The determination processes executed as a result of the determination processing program being executed constitute an example of the object determination method of the technique of the present disclosure. The processing performed by the determination processing program is similar to the DFT and determination performed by the determination device 220 of Embodiment 1, and thus, detailed descriptions thereof are omitted.

In step 270, the processing unit 252 sets a variable n indicating the number of times the power difference and angular difference have been calculated to 0, and in step 272, the processing unit 252 increments the variable n by 1.

In step 274, the processing unit 252 determines whether or not a prescribed number or greater of signals inputted by the ADC 204 to the computer 220C have been accumulated. If the prescribed number of signals has not been accumulated, then the determination of step 274 is executed until the prescribed number of signals is accumulated.

If the prescribed number of signals has been accumulated, in step 276, the DFT processing unit 254 executes the first DFT process for the prescribed number of signals, and determines the amplitude and phase of the first sine wave signal at the first frequency f1. Next, in step 278, the second DFT process is executed for the prescribed number of signals, and the amplitude and phase of the second sine wave signal at the second frequency f1 are determined.

In step 280, the power conversion unit 256 converts the amplitude of the signal at the first frequency f1 to a power value, and in step 282, the angle conversion unit 258 converts the phase of the signal at the first frequency f1 to an angle. In step 284, the power conversion unit 256 converts the amplitude of the signal at the second frequency f2 to a power value, and in step 286, the angle conversion unit 258 converts the phase of the signal at the second frequency f2 to an angle. In step 288, the power difference calculation unit 260 calculates the difference between the power value attained by conversion from the amplitude of the signal at the first frequency f1 and the power value attained by conversion from the amplitude of the signal at the second frequency f2. In step 290, the angular difference calculation unit 262 calculates the difference between the angle attained by conversion from the phase of the signal at the first frequency f1 and the angle attained by conversion from the phase of the signal at the second frequency f2.

In step 292, the processing unit 252 determines whether or not the variable n equals a total N. If it is determined that the variable n does not equal the total, then the determination process returns to step 272. If it is determined that the variable n equals the total N, then in step 294, the averaging unit 264 averages the power differences, and in step 296, the averaging unit 264 averages the angular differences.

In step 298, the determination unit 266 determines the properties of the soil according to the power difference, the angular difference, and the table shown in FIG. 5.

As described above, in Embodiment 2, the properties of the soil can be determined.

Embodiment 2 can be used as a landslide warning system or a plant growth system.

In Embodiment 2, it is possible to determine the properties of soil without a communication path between the transmission device 100B and the measurement device 200B for transmitting/receiving a timing signal pertaining to the phase of the signal generated by the transmission device 100B or a signal indicating level information of the transmission signal.

In Embodiment 2, it is possible to accurately determine the properties of soil even if external noise affects the signal transmitted/received.

Modification Examples

Next, modification examples of the technique of the present disclosure will be explained.

Modification Example 1

In Embodiments 1 and 2, the power difference and the phase difference were used, but a ratio of power values or a ratio of phases may instead be used, for example.

Modification Example 2

In Embodiments 1 and 2, the power value (amplitude) and the phase were used, but an amplitude change rate or a time difference corresponding to the phase may instead be used, for example.

Modification Example 3

In Embodiments 1 and 2, the timing at which to start generating the first sine wave signal is the same as the timing at which to start generating the second sine wave signal and the DFT timings are also the same, but a configuration may be adopted in which these timings differ from each other.

Modification Example 4

In Embodiments 1 and 2, the first sine wave signal has the same amplitude as the second sine wave signal, but a configuration may be adopted in which the amplitudes differ from each other. In such a case, when calculating the power difference, the power values are adjusted on the basis of the sizes of the differing amplitudes, and then the difference in power values is calculated.

Modification Example 5

In Embodiments 1 and 2, the power difference and the angular difference are averaged in order to reduce error. In other words, the amplitude and phase are acquired using signals received during the given periods for the DFT processes, and averages are calculated for a given number of amplitudes and phases, but a configuration may be adopted in which during the DFT process, one amplitude and one phase are acquired using a signal acquired during a given period×a given number of periods. In such a case, in Embodiment 1, the averaging circuits 216A and 216B are omitted, and the process of steps 270, 272, and 292 to 296 in Embodiment 2 is omitted.

Modification Example 6

In Embodiments 1 and 2, the properties of soil are determined, by way of example. However, embodiments of the present invention are not limited to soil, but the properties of another object may be determined. The properties of skin, other tissues, or the like may be determined, for example. The properties of other solids or fluids may also be determined.

Modification Example 7

In Embodiments 1 and 2, the amplitude is converted to a power value, but if the resistance in the device is large, the amplitude becomes low. However, by squaring the amplitude to convert it to a power value, the effect of error can be reduced. In Modification Example 7, the amplitude may be used without converting it to power.

Modification Example 8

In Embodiments 1 and 2, the first sine wave signal and the second sine wave signal are used, but instead of using sine wave signals, signals including, at a high proportion, unique frequency components that differ from each other may be used.

Modification Example 9

In Embodiments 1 and 2, a property of soil (first property) is determined using the first frequency $f1$ signal and the second frequency $f2$ signal. However, the technique of the present disclosure is not limited thereto. A third frequency $f3$ differing from the first frequency $f1$ and the second frequency $f2$, and a fourth frequency $f4$ differing from the first to third frequencies $f1$ to $f3$ may additionally be used. In such a case, a second table is provided in advance in which the properties of soil are identified and stored according to differences between the powers (amplitude squared) at the two differing frequencies $f3$ and $f4$, and differences between the phase angles of the signals at the two differing frequencies $f3$ and $f4$. Using the two different frequencies $f3$ and $f4$, a property of soil (second property) is determined in a manner similar to Embodiments 1 and 2. The final properties of the soil may be determined on the basis of the first property of the soil determined using the signal at the first frequency $f1$ and the signal at the second frequency $f2$, and the second property of the soil determined using the signal at the third frequency $f3$ and the fourth frequency $f4$. The final properties of the soil may be determined by calculating the average of the first property and the second property.

The properties of the soil may be determined using a plurality of sets of signals at the two different frequencies.

The plurality of sets of signals at the two frequencies include the following scenarios. In the case of two sets of signals, a set including the first frequency $f1$ and the second frequency $f2$, and a set including the third frequency $f3$ and the fourth frequency $f4$ can be included, for example. The two sets of signals may alternatively include a set including the first frequency $f1$ and the second frequency $f2$, and a set including the first frequency $f1$ and the third frequency $f3$.

In the case of three sets of signals, a set including the first frequency $f1$ and the second frequency $f2$, a set including the third frequency $f3$ and the fourth frequency $f4$, and a set including a fifth frequency $f5$ and a sixth frequency $f6$ can be included, for example. The three sets of signals may alternatively include a set including the first frequency $f1$ and the second frequency $f2$, a set including the first frequency $f1$ and the third frequency $f3$, and a set including the first frequency $f1$ and the fourth frequency $f4$.

Furthermore, in the case of four sets of signals, a set including the first frequency $f1$ and the second frequency $f2$, a set including the third frequency $f3$ and the fourth frequency $f4$, a set including the fifth frequency $f5$ and the sixth frequency $f6$, and a set including a seventh frequency $f7$ and an eighth frequency $f8$ can be included, for example. The four sets of signals may alternatively include a set including the first frequency $f1$ and the second frequency $f2$, a set including the first frequency $f1$ and the third frequency $f3$, a set including the first frequency $f1$ and the fourth frequency $f4$, and a set including the first frequency $f1$ and the fifth frequency $f5$.

The number of sets is not limited to two to four, and may be five or more.

DESCRIPTION OF REFERENCE CHARACTERS 100A transmission device
200A measurement device
208A power conversion circuit
208B power conversion circuit
210A angle conversion circuit
210B angle conversion circuit
212 power difference calculation circuit
214 angular difference calculation circuit
216A averaging circuit
216B averaging circuit
218 determination circuit
100B transmission device
200B measurement device
222 CPU
206 storage device
206A DFT unit
206B DFT unit
252 processing unit
254 processing unit
256 power conversion unit
258 angle conversion unit
260 power difference calculation unit
262 angular difference calculation unit
264 averaging unit
266 determination unit

What is claimed is:

1. An object-characteristic determination device for determining a property of soil, comprising:
    a calculation unit that calculates a first feature value of the soil and a second feature value of the soil differing from the first feature value according to a first signal at a first frequency and a second signal at a second frequency, the second frequency differing from the first frequency, the first signal and the second signal received by a reception unit after passing through the object, the first feature value and the second feature value representing features of the first signal and the second signal; and
    a determination unit that determines the property of the soil on the basis of a difference in the first feature values of the first signal and a difference in the second feature values of the second signal, a relationship between a plurality of properties of the soil, and a plurality of differences in the first feature values and a plurality of differences in the second feature values.

2. The object-characteristic determination device according to claim 1, wherein the differences in the first feature value and the differences in the second feature values are attained by subtraction.

3. The object-characteristic determination device according to claim 2, wherein the first feature value is an amplitude of the first signal and the second signal or a physical quantity related to the amplitude, and wherein the second feature value is a phase of the first signal and the second signal or a physical quantity related to the phase.

4. The object-characteristic determination device according to claim 3, wherein the calculation unit calculates an average of the first feature values calculated from the first signal and the second signal received during a plurality of first periods, and calculates an average of the second feature values calculated from the first signal and the second signal received during the plurality of first periods.

5. The object-characteristic determination device according to claim 3, wherein the calculation unit sets an entirety of a plurality of first periods as a second period and calculates an average of the first feature values received during the second period in the first signal and the second signal, and calculates an average of the second feature values received during the second period in the first signal and the second signal.

6. A method for determining a characteristic of soil comprising:
    calculating a first feature value and a second feature value, the second feature value differing from the first feature value, the first feature value and the second feature value based on features of a first signal and a second signal, the first signal having a first frequency and the second signal having a second frequency different from the first frequency, the first signal and the second signal received by a reception unit after passing through the soil; and
    determining a property of the soil based on a difference in the first feature values of the first signal and the second signal and a difference in the second feature values of the first signal and the second signal, based on a relationship between a plurality of properties of the soil, and based on a plurality of differences in the first feature values and a plurality of differences in the second feature values.

7. An object determination device, comprising: a non-transitory storage device that stores a program for causing a processing device to execute the object determination method according to claim 6; and
    the processing device that executes the program stored in the storage device.

8. A semiconductor device, comprising:
    a calculation unit that calculates a first feature value and a second feature value according to a first signal at a first frequency and a second signal at a second frequency, the second frequency differing from the first frequency, the second feature value differing from the first feature value, the first and second feature values representing features of the first signal and the second signal, and the first and second signals received by a reception unit after passing through soil; and
    a determination unit that determines a property of the soil on the basis of a difference in the first feature values and a difference in the second feature values of the first signal and on the basis of the first feature values and the second feature values of the second signal, on the basis of a relationship between a plurality of properties of the soil and on the basis of a plurality of differences in the first feature values and a plurality of differences in the second feature values.

* * * * *